United States Patent [19]
Zito, Sr.

[11] 4,331,160
[45] May 25, 1982

[54] METHOD FOR DETECTING AND RECORDING PHYSIOLOGICAL CHANGES ACCOMPANYING EMOTIONAL STRESSES

[76] Inventor: John J. Zito, Sr., 1527 Cottage La., Towson, Md. 21204

[21] Appl. No.: 929,907

[22] Filed: Aug. 1, 1978

[51] Int. Cl.³ ............................................. A61B 5/05
[52] U.S. Cl. ................................................. 128/734
[58] Field of Search ...................... 128/734, 735, 905; 346/33 ME

[56] References Cited

U.S. PATENT DOCUMENTS

| | | | |
|---|---|---|---|
| 2,535,249 | 12/1950 | Wilhelm et al. | 128/734 |
| 2,657,683 | 11/1953 | Koller | 128/734 |
| 2,661,734 | 12/1953 | Holzer et al. | 128/734 |
| 3,556,083 | 1/1971 | Grichnik et al. | 128/734 |
| 3,727,604 | 4/1973 | Sidwell et al. | 128/905 |
| 3,841,316 | 10/1974 | Meyer | 128/734 |
| 4,016,870 | 4/1977 | Lock | 128/735 |

*Primary Examiner*—Lee S. Cohen
*Attorney, Agent, or Firm*—Louis A. Scholz

[57] ABSTRACT

This invention relates to a device and method for detecting and recording a single electrical effect responsive to physiological changes accompanying emotional stresses, and in particular it relates to associated multiple stage amplifier circuits, having successive automatic zeroing devices and separate time responsive devices to eliminate or minimize physiological or biological electric potential drifts.

4 Claims, 5 Drawing Figures

METHOD FOR DETECTING AND RECORDING PHYSIOLOGICAL CHANGES ACCOMPANYING EMOTIONAL STRESSES

BACKGROUND OF THE INVENTION

There has been quite a bit of activity in the area of instruments for detecting and measuring electric effects responsive to physiological changes that accompany emotional stresses. One category of such devices is well known under the commonly used term "lie detectors." Historically, one of the pioneer instruments was developed in the 1920s by Dr. John A. Larson. It worked on the basis of simultaneously measuring blood pressure and respiration, and coupling the responses to recording pens writing on a traveling chart. Since most instruments record more than one physiological variation, they are usually called "polygraphs".

In the device disclosed herein attention is directed to electrical resistance variations between at least two spaced points on the skin of a person or other animal or mammal. Examples of such devices can be seen in the U.S. Pat. Nos. to Eilenberger 2,379,955, Wilhelm 2,535,249, Barnett 2,933,542, and Lukacs 2,638,401.

Most of these patents show one or more forms of electric amplifiers with individual "0" or zero settable means comprising either a D.C. voltage or an A.C. voltage across the electrodes as they are applied to the surface or skin of the test subject. By measuring the amount of current that flows after application of a specific voltage across the skin-flesh-skin path using the relationship expressed by Ohm's Law ($E=IR$), an indication of the test subject's unknown physiologically-induced resistance changes can be obtained. Usually this is done by what is known as a push-pull circuit similar to that shown in Lukacs U.S. Pat. No. 2,638,401. These are normally in the form of what is known as a bridge circuit so that the unknown varying resistance can be compared to a known or standard resistance and be expressed in terms of this relationship.

SUMMARY OF THE INVENTION

In the subject invention the electrodes are applied in a known manner to at least two points on the skin of person, organism or animal to be tested. A potential, preferably a D.C. voltage is applied across these electrodes, and through a bridge circuit in a known manner a measure is taken of the resistance and the variations of the resistance across these electrodes and through a portion of the subject test person. The output of this amplifier is then fed into a "NULL" or "0" level indicating means and level modifying means which is then, in turn, fed to a second stage amplifier or a second and third stage amplifier of known configuration which amplifier stage or stages have coupled with them a base line and sensitivity modifying means and whose outputs are terminated in perceivable means such as a suitable display. The base line and sensitivity modifying means then are manually changed at a specific time interval after each physiological interrogation, to "0" the input system to the electro-mechanical recording device or output perceiving means such as a moving pen and moving chart recording device. This device then provides a means of reading the electrical resistance changes in a particular path through a portion of a human or animal subject.

It is the purpose of this invention to provide by the combination or portions of it, disclosed herein, a device and method whereby the relationship between the resistance measured at the skin, and the body reaction to interrogations resulting in resistance changes of a subject person, are made evident on a recording mechanism. This relationship evidence is subject to being modified continuously at fixed time intervals by a "NULL" modifying means, so that the long term non-psychological changes or physiological "drifts" in bodily-induced resistance can be eliminated from the readings. Base line and sensitivity modifying means are used whereby the peculiar response of the tested subject to inquiry as recorded can be moved from time to time in position on the chart so that the chart's full range and full width can be utilized and matched to the response excursion range of the subject test resistance changes.

This allows for eliminating any "below zero" or negative excursion of resistance from the "NULL" point of balance. For the purposes of this invention, negative is explained to be below a certain level which is arbitrarily defined, in the output stages of the device as "zero". This is necessary because the device is essentially a bridge matching device, meaning one that matches the resistance of the test subject to that of a standard known resistance. When the device is being initially calibrated it is assumed that the subject's resistance will be substantially the highest, (response-indicating means the lowest) that it is going to be for the purposes of the remainder of the tests, thus giving the lowest current reading in the final stages of the amplifier. This being established as the base line or "zero", it is easily understood that if the subject's skin becomes drier during the test, the resistance would increase in value, and the amplified current would therefore decrease in value and a new low on the output of the chart or new "zero" would have to be established and vice versa.

This base line establishment has been done in the past by laborious calculations made after completion of the whole test by examining the tested person's resulting graph using calipers, and other measuring devices, to compute manually where the new low or new "zero" should be. In the subject device, a "zero" indicating and correcting means is supplied, so that in use, after each question and/or after each response, either verbal, physiological, or biological, a particular preset arbitrary time interval has been accomplished, the operator can manually or by automatic means shown herein, "zero" the base line. This together with the use of a base line position modifying means and a sensitivity modifying means allows the operator to diminish, if not almost entirely eliminate, any physiological and biological drift effect due to the long term variations in an individual being tested, and thus record in simplified graphical means a substantially uniform graphical representation on the same graphical scale of the psychological or biological resistance changes responsive to each of a series of questions. In other words, the system can automatically standardize each test.

DESCRIPTION OF THE DISCLOSED EMBODIMENT

Figure 1:
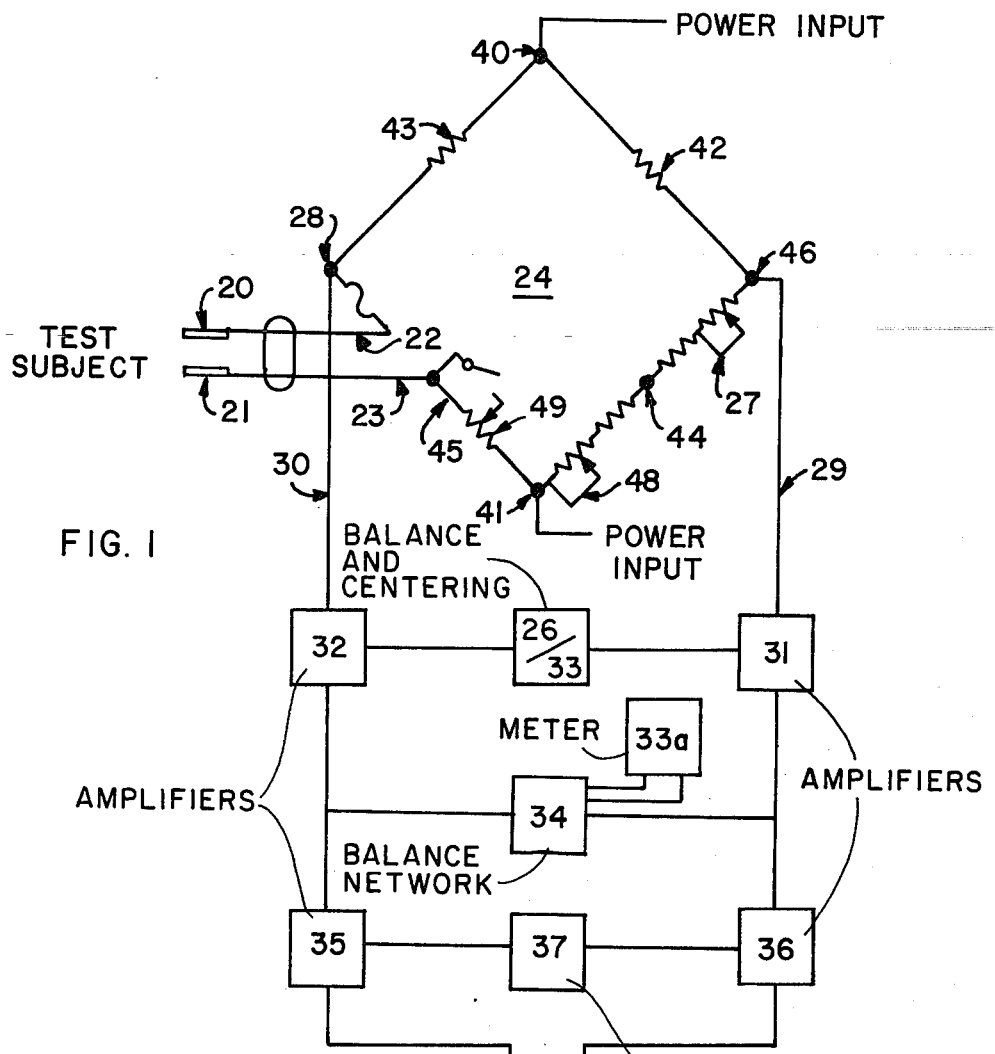
FIG. 1 shows a block diagram of the subject invention.
Figure 2:
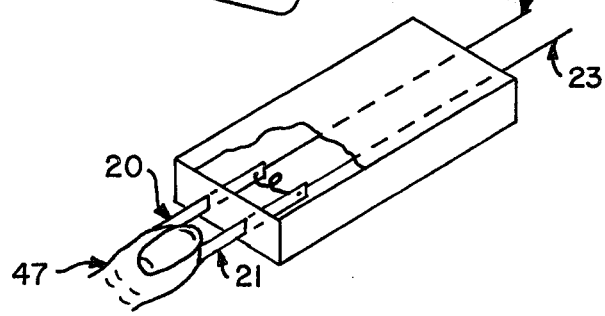
FIG. 2 is a perspective view of the skin electrodes as used.

As shown in FIG. 1, the variations in biological resistance are conducted to a gap in one leg of a bridge circuit. This bridge circuit 24 is fed from test electrodes 20 and 21 placed at two points in spaced relation on a portion of the body, such as the finger 47, FIG. 2, of the person whose psychological response is to be measured. The circuit is continued through conductors 22 and 23 and is provided with balancing and calibrating resistances and whose effect is read on meter 33a balance circuit 34. The output of this Wheatstone-type bridge circuit is fed through conductors 29 and 30 from bridge junction points 28, 46 to the first stage amplifier means 31 and 32, which are in turn connected commonly through an amplifier balancer 33 and read out balance circuit 34. A centering control circuit 26 interconnects amplifiers 31 and 32. The output of the first stage amplifiers 31 and 32 are fed across a meter calibration and read out circuit 34 which is used initially to calibrate the equipment. The meter is not employed for testing circuits to the second stage amplifiers 35 and 36 which have a base line and sensitivity circuit connected between them at 37.

Figure 3:
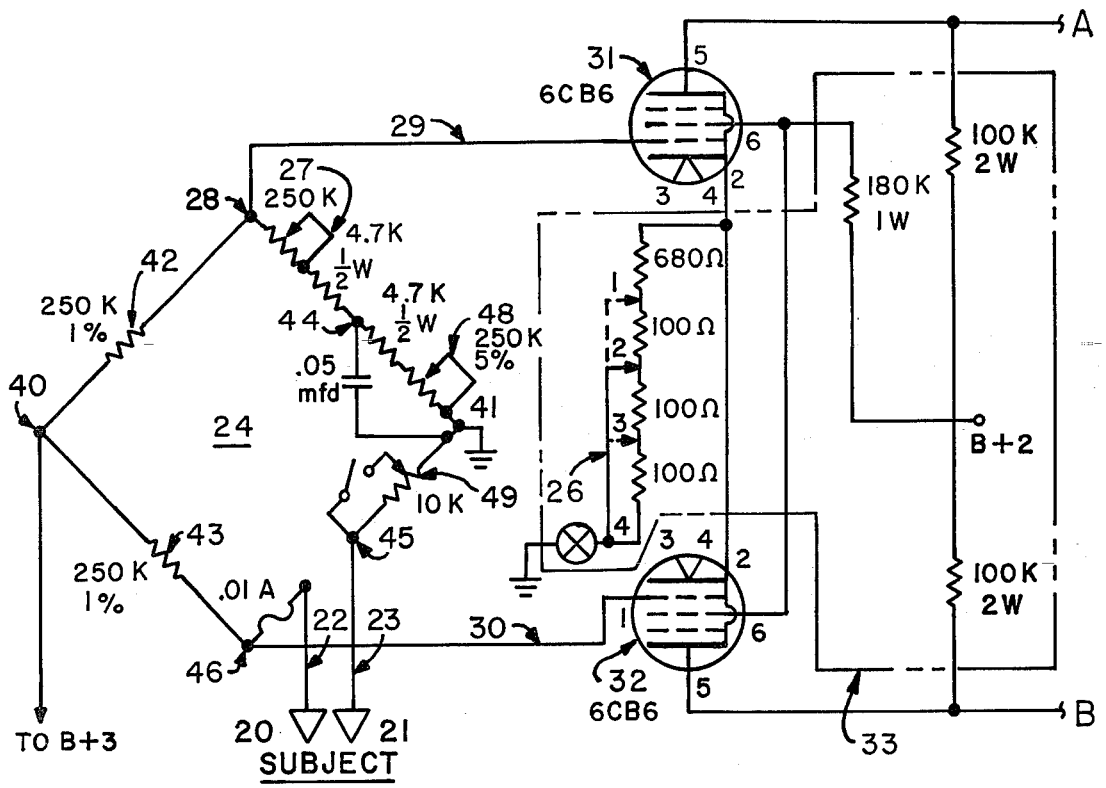
FIG. 3 shows a two-stage amplifier system or network connected to a bridge "output" which in turn is connected to a pair of electrodes showing a direct coupled amplifier system for amplifying test resistance variations to a level high enough to actuate a penned recording mechanism or other perception means which mechanisms record the resistance variations.
Figure 3:
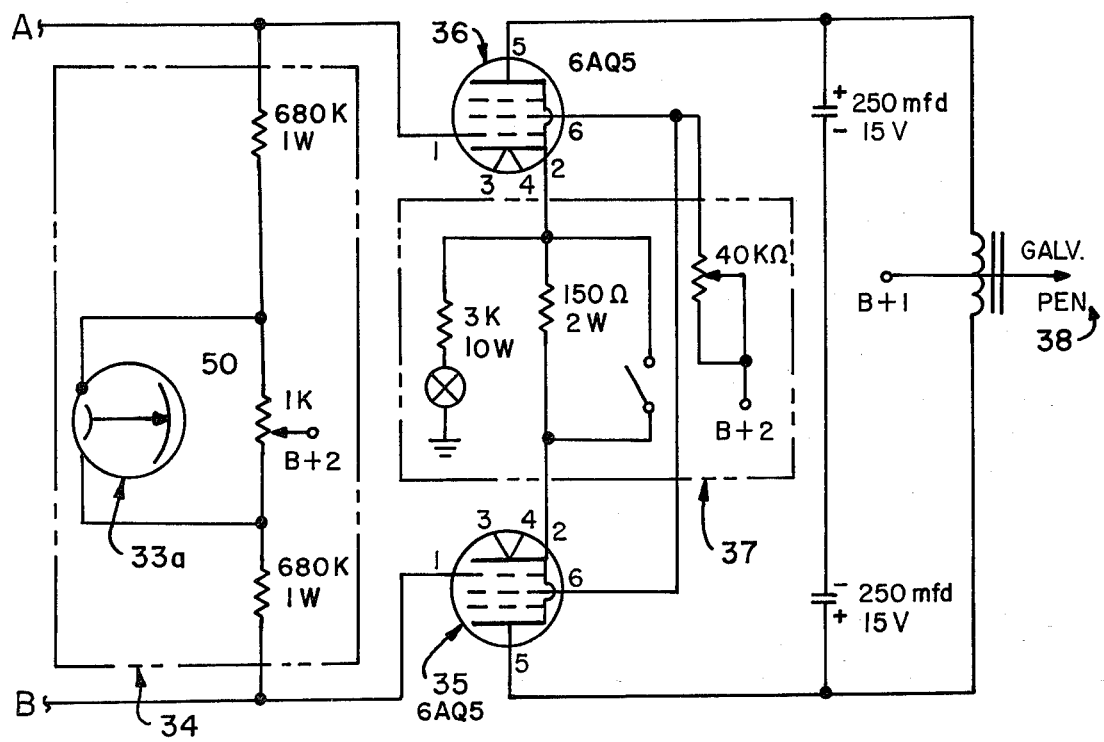

The output of the second stage amplifiers 36 and 35 is fed into the automatic pen 38 or similar recording device, and recorded on moving chart 39 or on any cathode ray tube or digital read-out devices, which read-out devices are readily available and known in the market. A specific example of such a circuit with illustrative component values is shown in FIG. 3. FIG. 3 shows a modified Wheatstone bridge circuit 24 having typically four conducting arms with electrodes 20 and 21 applied to the test subject and the conventional power input to the bridge being applied at conductor junctions 40 and 41 in the circuit as shown. This is preferably a DC power input. The first two like arms of the bridge with fixed resistors 42 and 43 have substantially identical resistances of high value to minimize current drains. The third and fourth arms of the bridge 44 and 45 are characterized by the fact that arm 45 has a break in it for the electrodes 20 and 21 connected across the break as by conductors 22 and 23, and additionally in that leg of the bridge is a deviation test switch with a variable resistor 49 that is adjusted initially to make an amplifier performance check. The fourth leg of the bridge 44 has a balance range control variable resistor 27 and centering control variable resistor 48.

The output of the bridge is conducted through conductors 29 and 30 conducting the output from the two legs of the bridge 44 and 45 at 46 and 28, respectively, into first stage amplifiers 31 and 32. In this case the input being fed into an amplifier such as the grid of a vacuum tube. In a known manner the output of the amplifier units 31 and 32 are balanced by plate resistor network 33. This amplifier output from the plates of the vacuum tubes, in turn, is then fed to the balance meter 33a and associated meter calibration circuit 34. The balancing circuit is similar to those already known in the art. The then balanced output of the first stage amplifier having been meter-balanced is then fed into second stage amplifiers 35 and 36. In this stage, a center base line switch and sensitivity circuit 37 is connected between the control plates of the vacuum tube amplifier. The center base-line switch and sensitivity control circuit 37 is used both to set the range or sensitivity of the swing of the output, and the position of the center line. Also the outputs from amplifiers 36 and 35 are fed into the operating coil of a galvanometer recording pen, or to the input of a cathode ray tube or digital display device.

In the operation of the device when used for so-called "lie-detecting" it is important to adjust the pen response by varying the centering control 26 on the input from the bridge circuit and by observing the meter 33a. This is independent of the amplifier gain or sensitivity. In operation, after the electrodes 20, 21 have been applied in spaced relation to the two points on the test subject, the amplifier system is allowed to be balanced out by the balance range control 27 and the centering control 26 with the test subject resistance in the circuit. The test is observed and by varying the final output sensitivity control 37 the excursion or variation of the pen 38 can be kept within the bounds of the chart limits. The testing proceeds to achieve objective uniformity by zeroing the balance meter 33a a definite time prior to each question, such as 3 to 20 seconds after the question has been asked.

This use of a separate zeroing control is unique in devices of this type. By zeroing the device in the bridge circuit a fixed time after each question is asked, such zeroing takes out the individual emotional drift or excursion from question to question and provides a uniform base line against which all questions can be compared. This greatly simplifies the analysis of the response of the person being tested.

Figure 4:
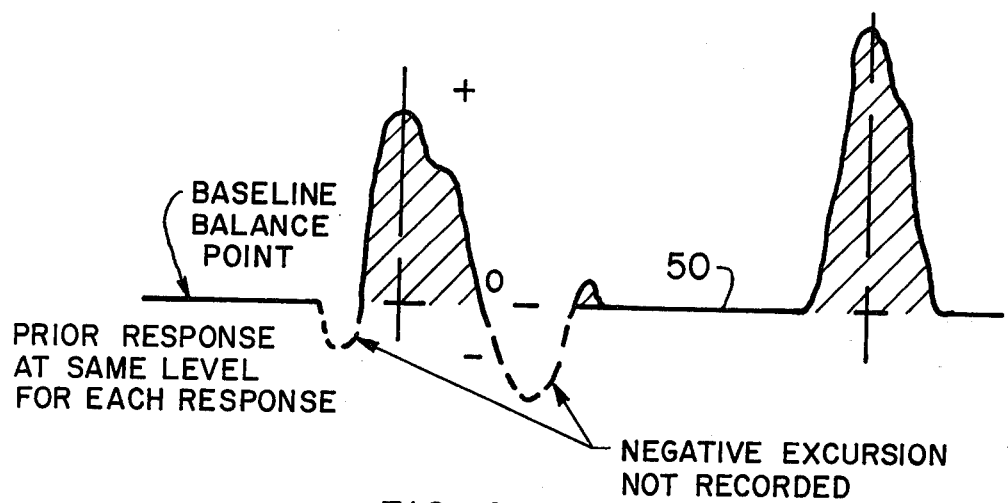
FIG. 4 is a diagrammatic chart produced by the invention.
Figure 5:
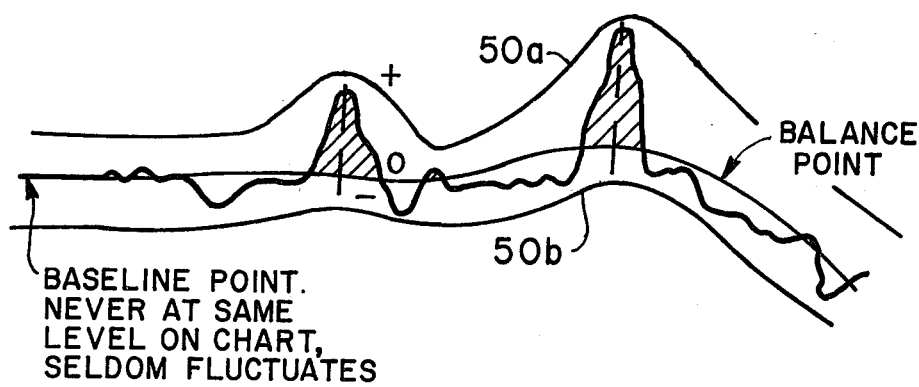
FIG. 5 is a diagrammatic illustration of a response charge as produced by the prior art.

Examples of charts made by the subject invention are shown in FIG. 4 showing readings having a fixed base line at 50 from continuous corrections. In FIG. 5, a conventional analysis or curve from the same subject response as shown in FIG. 3 is shown without the automatic base line correction with superimposed drift guide lines 50a and 50b to show the mathematical type conversion that must be done in order to successfully analyze a full curve without the base line correction.

The double balancing method, that is a sensitivity adjustment and also a specific question time-related meter balance adjustment is unique in the measuring of the skin response. This greatly simplifies and improves the detection of real psychological variations as opposed to a test subject's psycholological or physiological drift variations.

While I have shown the invention as employed with vacuum tube circuits, it is of course within the spirit and scope of the invention to employ common equivalent circuit components therefor, as transistors, integrated circuits and the like.

What is claimed is:

1. A method of indicating variations in resistance across a portion of a living being comprising the steps of:
    connecting a pair of electrodes in spaced relation across said portion of a living being and into one arm of a Wheatstone bridge, thereby to complete the circuit through said arm with said living being,
    providing a variable resistance in a second arm of the bridge,
    amplifying the outputs of the two bridge arms to provide amplified outputs therefor, connecting a measurement display means to the said amplified bridge outputs to show the condition of the living being, initially balancing the said amplified outputs to a null condition by adjusting said variable resistance while the electrodes are in contact with the living being and prior to a predetermined test sequence to be administered to the living being, thereafter successively rebalancing the outputs to an indicated null condition while the electrodes are in contact with the living being at predetermined timed intervals following each response of the living being during the predetermined test sequence, interrogating the living being as a portion of the said test sequence, and, displaying the determined condition of the living being on the measurement display means over a period of time during said test sequence.

2. The method of claim 1 including the step of exhibiting in spaced relation on said display means the repetitive nulled condition of the bridge and further exhibiting on said display means successive variations therefrom of the condition of the living being between said indicated null conditions.

3. The method of claim 1 including the step of connecting a cathode ray tube to said outputs as said display means.

4. The method of claim 1 including the step of connecting a chart recorder to said outputs as said display means.

* * * * *